(12) United States Patent
Mehta et al.

(10) Patent No.: US 9,993,584 B2
(45) Date of Patent: Jun. 12, 2018

(54) NASAL ASPIRATOR

(71) Applicant: NeilMed Pharmaceuticals, Inc., Santa Rosa, CA (US)

(72) Inventors: Ketan C. Mehta, Santa Rosa, CA (US); Srikanth Pai, Santa Rosa, CA (US)

(73) Assignee: NeilMed Pharmaceuticals, Inc., Santa Rosa, CA (US)

( * ) Notice: Subject to any disclaimer, the term of this patent is extended or adjusted under 35 U.S.C. 154(b) by 551 days.

(21) Appl. No.: 14/643,822

(22) Filed: Mar. 10, 2015

(65) Prior Publication Data
US 2016/0263295 A1 Sep. 15, 2016

(51) Int. Cl.
*A61M 1/00* (2006.01)

(52) U.S. Cl.
CPC .......... *A61M 1/0003* (2013.01); *A61M 1/0072* (2014.02); *A61M 2205/075* (2013.01); *A61M 2205/076* (2013.01); *A61M 2210/0618* (2013.01)

(58) Field of Classification Search
CPC .............. A61M 1/0003; A61M 1/0072; A61M 2205/075; A61M 2205/076; A61M 2210/0618
See application file for complete search history.

(56) References Cited

U.S. PATENT DOCUMENTS

| | | | |
|---|---|---|---|
| 5,062,835 A | 11/1991 | Maitz et al. | |
| 5,800,425 A * | 9/1998 | DeLeonardis | A61M 1/0023 600/573 |
| 9,144,635 B1 * | 9/2015 | Kaplan | A61M 1/0009 |
| 2011/0319840 A1 | 12/2011 | Hair | |
| 2012/0029486 A1 * | 2/2012 | Laerdal | A61M 1/0003 604/540 |

FOREIGN PATENT DOCUMENTS

| | | |
|---|---|---|
| CN | 2860472 | 1/2007 |
| WO | WO 03/035144 | 5/2003 |

OTHER PUBLICATIONS

Authorized officer Bong Ho Chang, International Search Report and Written Opinion in PCT/US2015/023508, dated Dec. 4, 2015, 11 pages.

* cited by examiner

*Primary Examiner* — Benjamin Klein
(74) *Attorney, Agent, or Firm* — Kelley Drye & Warren LLP

(57) ABSTRACT

An aspiration device is described, including a bulb aspirator including a bulb body, a first collar and tip, the bulb body includes an upper portion configured for receiving one end of the first collar and lower portion configured for receiving in a first configuration a stop and in a second different configuration a second collar associated with a suction tube, the tip is configured for insertion into a passageway; the stop being configured for detachable connection to the lower portion of the bulb body when in the first configuration; and the suction tube including the second collar, a tube portion and an adaptor, the second collar is disposed at a first end of the suction tube and being adapted to be coupled to the lower portion of the bulb body, the adaptor is configured to adapt to a human mouth to enable suction to be applied at the adaptor.

11 Claims, 7 Drawing Sheets

NASAL ASPIRATOR

FIELD

This disclosure relates to nasal aspirator systems.

BACKGROUND

Nasal aspirator systems are commonly used in the cleansing of a human's or any other animal's nostrils. For example, babies lack the ability to clear their own nostrils with great efficiency, so that blockage in the nostrils can remain for extended periods of time, impairing breathing, eating, breast feeding, and mood. Due to the frequency of a runny or congested nose, parents may purchase nasal aspirators of various types and functionalities. One common nasal aspirator is a rubber bulb that includes a tip which may be inserted into a baby's nostril. The squeezing of the bulb pushes air from the bulb through the tip. Release of the bulb creates a low (i.e., negative) pressure area in the bulb, bringing air (and potentially mucus) through the tip and into the bulb and will result in equalizing the pressure (a return to a neutral state) when the bulb is re-inflated due to elasticity. This equalization process creates a suction from the tip and quite literally sucks out mucus or nasal secretions from the nostril (assuming the tip has been placed there at the time of release).

SUMMARY

Systems and methods for nasal aspiration are described. In some implementations, an aspiration device is provided that includes a bulb aspirator portion including a bulb body, a first collar and tip, wherein the bulb body includes an upper portion configured for receiving one end of the first collar and lower portion being configured for receiving in a first configuration a stop and in a second different configuration a second collar associated with a suction tube, wherein the tip is configured for insertion into a passageway and being tapered and angled in shape for ease of insertion and conformity to a respective cavity; the stop being configured for detachable connection to the lower portion of the bulb body when in the first configuration; and the suction tube including the second collar, a tube portion and an adaptor, wherein the second collar is disposed at a first end of the suction tube and being adapted to be coupled to the lower portion of the bulb body, wherein the adaptor being coupled to the second end of the suction tube and being configured to adapt to a human mouth to enable suction to be applied at the adaptor so as to enable the application of a suction through the suction tube and into the bulb aspirator when the tube portion is coupled to the bulb aspirator in the second different configuration.

Particular embodiments of the subject matter described in this specification can be implemented so as to realize zero or more of the following advantages. A described nasal aspirator system can have accurate, fine-tuned control of suction through the nasal aspirator system. The nasal aspirator system can include a tip inserted into a baby's nostril, with another end inserted into a parent's mouth. The parent can have accurate control of an amount of suction by regulating their own lungs and depth and speed of breath. The described nasal aspirator system is therefore much safer than previous aspirator systems since a parent can precisely control the suction and stop instantaneously (as required). One or more filters in the nasal aspirator system are included to block any mucus or secretions (or any other particulate matter) that is sucked out of the nostril. The described nasal aspirator system also substantially blocks the flow of air back out of the tip when used in the suction mode, using a one way valve, so that there is no danger of accidentally blowing air through the nasal aspirator system back into the nostril. When configured with a one way valve, the device can also be used to suction out a (e.g., accidentally) placed foreign body in a nostril (such as by a child). Examples of foreign bodies include toys or toy parts (such as a small marble) or food items including nuts, seeds and fruits or other small items that may become lodged in a nostril.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

Figure 1:
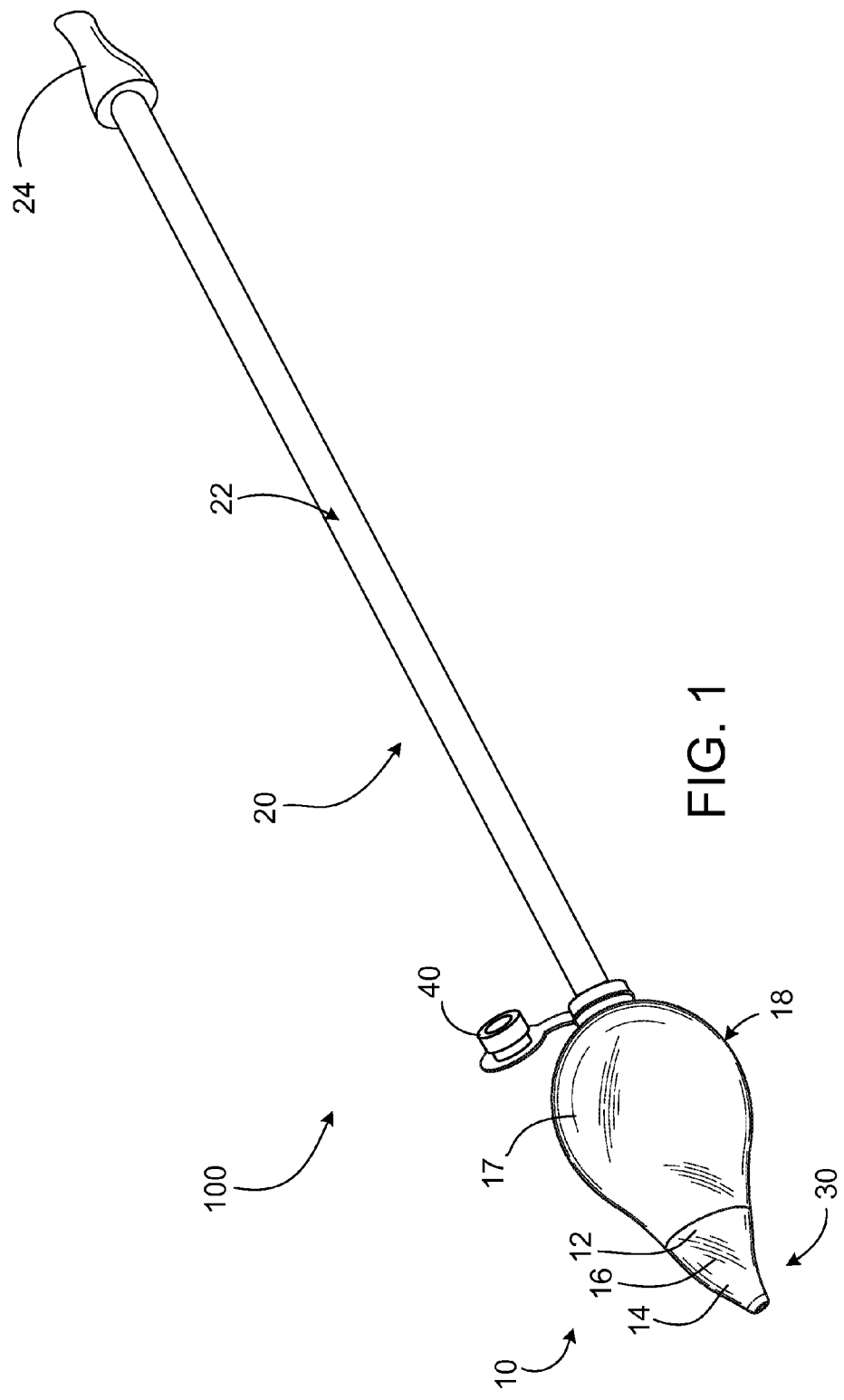
FIG. 1 is a schematic perspective view of an example aspirator device.

Referring to FIG. 1, an example of an aspirator device 100 is shown. The aspirator device 100 includes a bulb aspirator 10 coupled to a suction tube 20.

The bulb aspirator 10 includes a bulb body 12 configured to receive a removable first collar 14 at an upper portion 16. The first collar 14 is also configured for a detachable connection with a tip 30, which can be inserted into an orifice e.g., a nostril of an adult or baby. The bulb body 12 includes a lower portion 17 that is further configured to receive a stop 40 in a first configuration, and the suction tube 20 in a second configuration.

The suction tube 20 includes a tube portion 22 for the flow of a gas or fluid or combination of these, with the second collar 18 disposed at an end of the tube portion 22. An adaptor 24 can be coupled to the opposite end of the tube portion 22, and is configured to adapt to a human mouth. The adaptor 24 allows for suction to be created by a human, which forces air through the adaptor 24 in a first direction into the mouth. Additionally, in some implementations the adaptor 24 is configured to substantially inhibit air being pushed into the adaptor 24, substantially blocking an opposite (e.g., second different) direction flow of air out of the mouth and back into the tube portion 22. In some implementations, a one way valve may be included in the adaptor 24 or disposed at another location in the bulb aspirator 10.

In the first configuration, e.g., the configuration with the stop 40 inserted into the bulb body 12 at the lower portion 17, a human can deform the bulb body 12, e.g., by squeezing the bulb body 12, expelling air inside the bulb body 12 through the tip 30. The tip 30 may then be inserted into an orifice, e.g., a baby's nostril, and the deformed bulb body 12 may be released which in turn causes air and particulate matter, e.g., mucus, to be suctioned into the bulb body 12 through the tip 30.

In the second configuration with the suction tube 20 attached to the bulb aspirator 10, a human can create a suction through the adaptor 24 and control the suction by adjusting a pressure differential between atmospheric pressure (as presented at the tip of the bulb aspirator) and pressure in a space associated with a person's body such as by creating a negative pressure to initiate the act of suction, e.g., induced by activating muscles in the mouth and diaphragm to rapidly increase the space of air inside the human's body. The pressure differential will then force air through tip 30, bulb body 12, suction tube 20, and out of the adaptor 24 into the human. Since the human can control the suction, and thus the airflow through the aspirator device 100, the human can insert the tip 30 into a baby's nostril and have great control over the suction induced in the delicate nostril.

Figure 2:
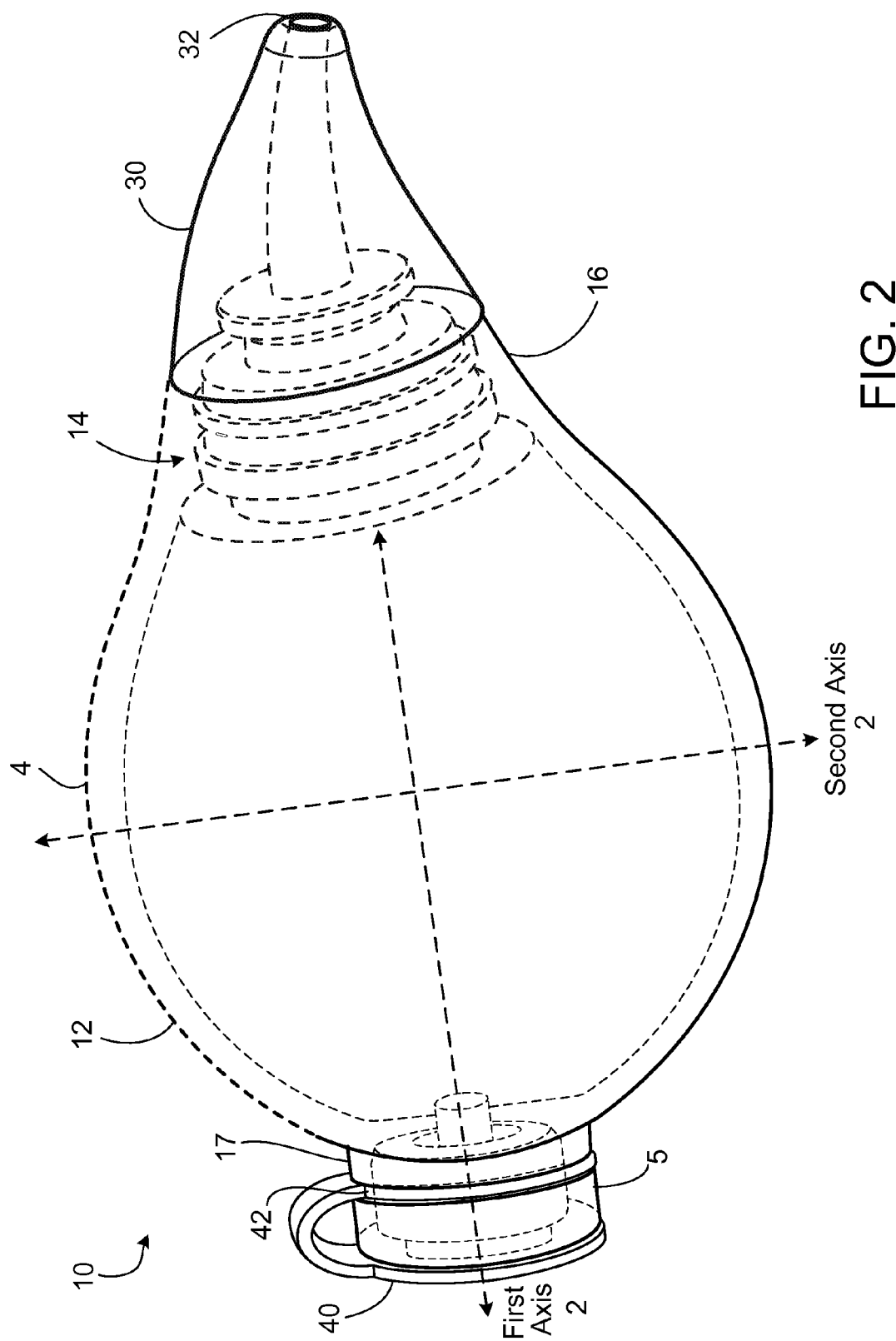
FIG. 2 is a schematic view of the example bulb aspirator in a first configuration.

FIG. 2 is a schematic view of the bulb aspirator 10 in a first configuration. As described above, the bulb aspirator 10 includes a bulb body 12, a first collar 14, and a tip 30. The first configuration of the bulb aspirator 10 includes the bulb aspirator 10 with a stop 40 inserted into the lower portion 17 of the bulb body 12. When positioned in the lower position of the bulb body, the stop 40 can allow for a pressure differential to be created through a squeezing and releasing of the bulb body 12, e.g., by blocking the flow of air out of the lower portion 17.

In some implementations, the bulb body 12, included in the bulb aspirator 10, is generally made of a deformable material, e.g., a human hand can deform the bulb body 12. In some implementations the bulb body 12 can be made of a clear plastic, e.g., a high grade silicone plastic, that can contain air, fluids and particulate matter that passes through, or remains in, the bulb body 12. The clear plastic that defines the shape of bulb body 12 can be substantially 2, 2.5, or 3 mm thick and the interior of the bulb body 12 can be hollow to hold air, fluids or solids, e.g., air, mucus.

In some implementations, the bulb body 12 is generally symmetric about a first axis 1, and can be substantially 50 mm, 55 mm, or 60 mm, along the first axis 1. Additionally, in some implementations, a mid-section of the bulb body 12 can be substantially 40 mm, 48 mm, or 54 mm, along an orthogonal second axis 2. In some implementations, the bulb body 12 tapers down along the second axis 2 as the body extends farther from the mid-section along the first axis 1, reaching the extremities of the bulb body, e.g., the upper portion 16 and the lower portion 17 described below.

The bulb body 12 can be described as roughly a spheroid, e.g., an oblate spheroid, with an upper portion 16 at an extremity of the bulb body 12, and a lower portion 17 at an opposite extremity of the bulb body 12. The lower portion 17 and upper portion 16 are hollow cylinders extending from the spheroid with respective openings at extremities of the bulb body 12.

The absolute value of the derivative of the arc length 4 along the second axis 2 of the bulb body 12 with respect to the first axis 1 can be relatively constant, from the lower portion 17 to the upper portion 16 of the bulb body 12. The derivative of the arc length 4 can decrease at a distance from the opening of the upper portion 16 and the opening of the lower portion, e.g., substantially 5 mm, 7 mm, 9 mm. This decreased derivative creates a substantially flat cylinder attached to either side of the spheroid of the bulb body 12. The cylinder of the upper portion 16 allows for both a connection with the first collar 14, and for a human to rest his/her thumb or fingers on the cylinder when in use in the first configuration.

The cylinder of the lower portion 17 allows for a connection with the stop 30 in the first configuration, as illustrated in FIG. 2. The lower portion 17 includes a first end of a neck region 5, e.g., the opening, and a second opposite end of the neck region 5, e.g., adjacent to the spheroid of the bulb body 12. The neck 5 can define the cylinder of the lower portion 17 and can be a particular distance along the first axis 1, e.g., substantially 4 mm, 8 mm, or 12 mm. In some implementations, the neck region can be recessed so as to enable a substantially flat bottom of the bulb body 12 at the lower portion.

The stop 40 includes a cap that is of a similar or greater radius as the opening of the bulb body 12, and an elongated portion that extends from the cap. The elongated portion of the stop 40 is adapted to be inserted into the neck 5 through the opening of the bulb body 12, and rest (and be maintained) inside the neck 5. The radius of the elongated portion is selected so as to put pressure on the neck 5, which creates a seal blocking the flow of air through the opening, such as when the bulb body 12 is deformed when used in the first configuration.

The neck region 5 includes an external circumferential recess, which can hold a ring 42 attached to the stop 40. As illustrated in FIG. 2, the ring 42 attached to the stop 40 can hang from the circumferential recess, keeping the stop 40 connected to the bulb body 12 when inserted into the bulb body 12, or when not inserted. Other means for retaining the stop when in use or not in use are possible.

The external circumferential recess creates an internal circumferential ridge in the neck 5. In some implementations, the stop 40 can include a corresponding circumferential recess on the elongated portion, which can receive the internal circumferential ridge of the neck 5. In this way, the stop 40 can be locked to the neck 5, which helps to create a seal to block the flow of air through the opening of the bulb body 12.

The bulb body 12 has an opening at the upper portion 16 that is configured to receive the first collar 14. The upper portion 16 includes internal circumferential ridges (e.g., a first ridge separated from a second ridge of a different size) that are configured to receive ridges included on the outside of the first collar 14.

In some implementations, the first collar 14 can be made of a hard plastic, e.g., poly propylene, and include a hollow passageway for the flow of air, fluids and particulate matter. The first collar 14 has ridges that are opposite to the internal ridges in the upper portion 16, e.g., to lock the ridges of the first collar 14 to the internal ridges of the upper portion 16. In this way a user can insert the first collar 14 into the upper portion 16 to attach the first collar 4.

In some implementations, a portion of the first collar 14 remains outside of the bulb body 12 when inserted. This portion of the first collar 14 is configured to be inserted into a distal end of the tip 30, connecting the bulb body 12 with the tip 14 via the respective connections with the first collar 14.

The distal end of the tip 30 includes one or more internal ridges that can connect to the portion of the first collar 14 (e.g., that remains outside the bulb body 12). The ridges of the tip 30 can be formed such that when a human pulls on the tip 30 after connecting it to the first collar 14, the tip 30 will not come loose without sufficient force. The detachable portions of the first collar 14, tip 30 and bulb body 12 allow for easy cleaning and or sterilization of the respective components. Similarly, the use of transparent materials for the bulb body 12 and tip 30 allow for visual inspection of the aspirator device 100 once assembled.

The tip 30 is configured with an internal hollow nozzle, with an opening 32 at the proximate end that can pass air, fluid and particulate matter through the hollow passageway of the first collar 14 and into the hollow bulb body 12 upon an application of a suction force e.g., by deformation of the body in the first configuration or by a human in the second configuration. The opening 32 of the tip 30 is angled to be inserted comfortably into a cavity (e.g., a nasal cavity of a human adult, child or a baby. The angle can be determined, for example, from an examination of the shape of an average baby's nasal cavity. Additionally the radius of the internal hollow nozzle of the tip 30 can be of a sufficiently small size so as to allow the ease of ingress of the tip 30 into a human's nostril, e.g., substantially 2 mm, 4 mm, or 5 mm.

Additionally, the tip 30 can be made of a deformable material. The deformable material can be of the form of silicon rubber, such as for comfort when being inserted in the nostrils of a human, e.g., a baby.

Figure 3A:
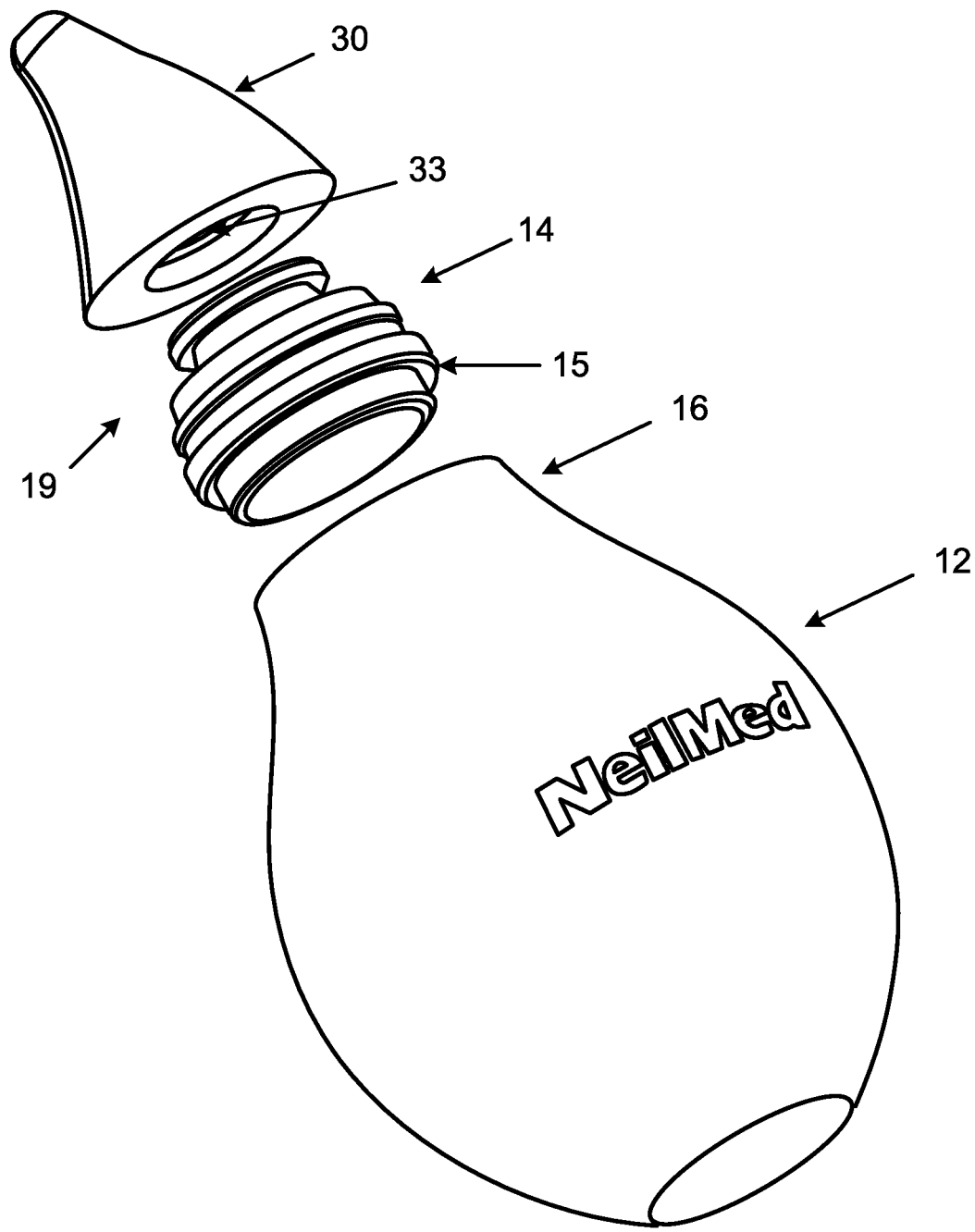
FIG. 3A is a schematic view of an example of the external ridges of the first collar, and a connection of the tip to the first collar and the first collar to the bulb body.

FIG. 3A is a schematic view of the external ridges 15 of the first collar 14, and a connection of the tip 30 to the first collar 14 and the first collar 14 to the bulb body 12. The first collar 14 can detachably connect to the tip 30 by an insertion of the first collar 14 into the tip 30, and the first collar 14 can detachably connect to the bulb body 12 by an insertion of the first collar 14 into the bulb body 12. Other means of connecting are possible (press fittings, sleeves or the like).

Figure 3B:
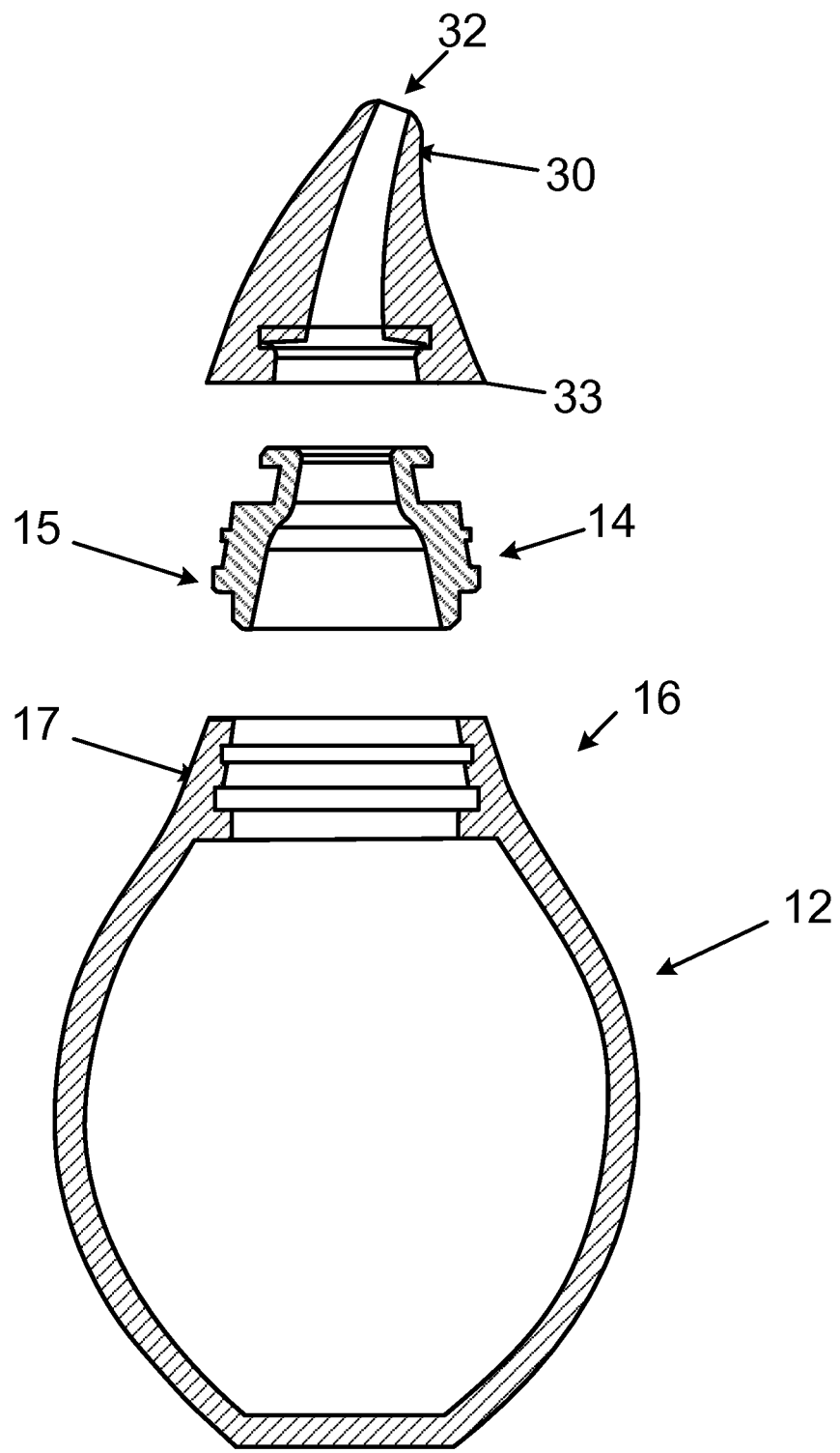
FIG. 3B is a schematic view of an example of the internal ridges of the tip and the bulb body.

The tip 30 includes internal ridges 33, described in FIG. 3B, that are complementary to the ridges 15 of the detachable first collar 14. A complementary ridge is a ridge that is of about opposite height to a different ridge such that the ridges can interlock. As illustrated, the ridges 15 extend from a tapering cylinder 19, e.g., tapering toward the distal end of the tip 30, that describes the basic form of the first collar 14. The ridges 15 are of varying heights with respect to the tapering cylinder 19, such that when rested against the complementary internal ridges 33 in the tip 30, a seal is created. The first collar 14 connects to the tip 30 via one or more ridges 15 of the first collar 14 that extend from the bulb body 12 when the first collar 14 is inserted into the bulb body 12.

In implementations where the tip 30 is made of a deformable material, the tapering cylinder 19 of the first collar 14 can be of sufficient radii to put pressure on the internal ridges 33 of the tip 30 when inserted. In this way the first collar 14 can be held in place by pressure, in addition to the respective complementary ridges in the tip 30 and first collar 14.

The bulb body 12 can receive the first collar 14 by an insertion of the first collar 14 into the upper portion 16 of the bulb body 12. The bulb body 12 includes internal ridges, described in FIG. 3B, that can receive the external ridges 15 of the first collar 14. The radius of the upper portion 16 of the bulb body 12 can be of a sufficiently small radius with respect to the radii 15 of the tapering cylinder 19 of the first collar 14 so as to create pressure between the bulb body 12 and first collar 14 when inserted.

One or more of the external ridges 15 of the first collar 14 are configured to be inserted into the bulb body 12, with one or more of the external ridges 15 configured to remain outside of the bulb body when the first collar 14 is inserted. To effect this, the internal ridges of the bulb body 14, described in FIG. 3B, can be complementary to less than the full amount of external ridges 15 of the first collar 14. In this way, when the first collar 14 is inserted, external ridges 15 that lack complementary internal ridges in the bulb body 12 will remain outside of the bulb body 12.

As described above, the external ridges 15 remaining outside of the bulb body 12 are configured to be inserted in the tip 30. While reference is made to the tip and the bulb body have a particular size and configuration (such as to enable separation of the two individual pieces to enable cleaning of the inside of the bulb body), the point of separation that is associated with the first collar may be at any of a variety of locations on the bulb body as required.

FIG. 3B is a schematic view of the internal ridges of the tip 30 and the bulb body 12. As described above, the bulb body 12 is configured to receive the first collar 14, and the tip 30 is configured to receive the first collar 14.

The tip 30 includes one or more internal ridges 33, e.g., internal circumferential ridges, with each ridge receiving a connection with a complementary external ridge 15 of the first collar 14.

The bulb body 12 includes one or more internal ridges 17, e.g., internal circumferential ridges, with each ridge receiving a connection with a complementary external ridge 15 of the first collar 14.

As illustrated in FIG. 3B, the first collar 14 includes two external ridges 15 that can be inserted into complementary internal ridges 17 of the bulb body 12. The first collar 14 also includes a third external ridge 15 that can be inserted into a complementary internal ridge 33 of the tip 30. In this way the first collar can connect the bulb body 12 to the tip 30. The bulb body 12 is therefore flush with the distal end of the tip 30, creating a continuous path on an exterior surface of the bulb aspirator 10 from the proximate end of the tip 30 to the opposite side of the bulb body 12.

After the tip 30 is connected to the bulb body 12, a continuous path for air, fluid and particulate matter flow is created that extends from the hollow nozzle 32 of the proximate end of the tip 30, through the first collar 14, and into the bulb body 12. The interlocking connections between the tip 30 and the first collar 14, and the first collar 14 and the bulb body 12, create a seal that keeps the flow of air, fluid and particulate material contained in the bulb aspirator 10.

Figure 4:
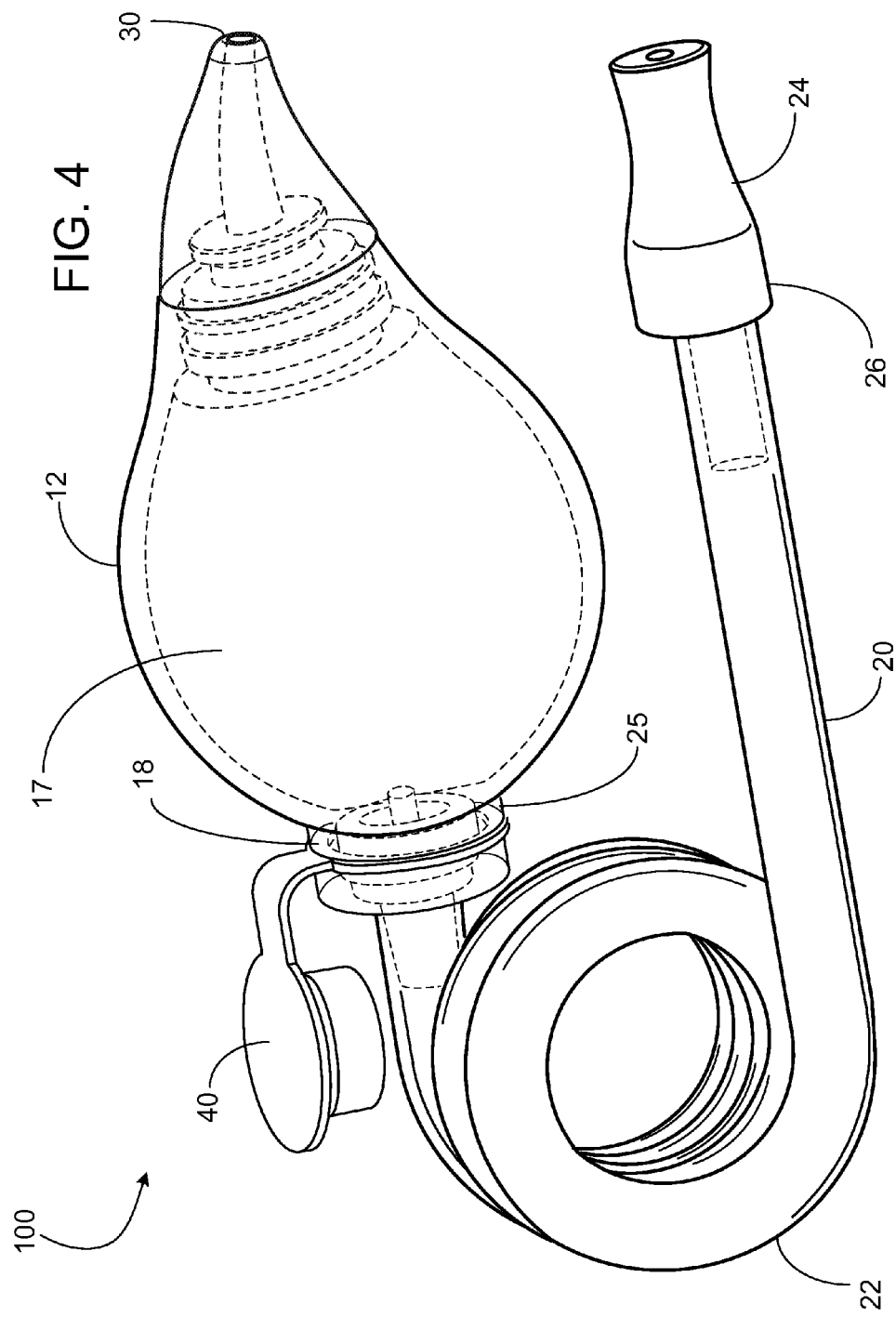
FIG. 4 is a schematic view of the example bulb aspirator in a second configuration.

FIG. 4 is a schematic view of the bulb aspirator 10 in a second configuration. As described above, the aspirator device 100 includes a bulb aspirator 10 and a suction tube 20 configured to be coupled to the bulb body 12 of the bulb aspirator 10. In the second configuration, the bulb body 12 of the bulb aspirator 10 is coupled to the suction tube 20, allowing for the suction, e.g., suction created from a human's mouth applied to the adaptor 24, of particulate matter, e.g., mucus from a baby's nose, from the tip 30 into the bulb body 12.

A second collar 18 is adapted to be detachably inserted into the lower portion 17 of the bulb body 12, and further adapted to be detachably inserted into the tube portion 22 of the suction tube 20.

The second collar 18 can be created from a hard plastic, e.g., poly propylene, that can be inserted into the lower portion 17 of the bulb body 12. As described above, the bulb body 12 can be constructed from a deformable material, which can be stretched around the second collar 18. The second collar 18 can therefore be inserted into the lower portion 17 of the bulb body 12, and be held in place by pressure created between the second collar 18 and bulb body 12. In some implementations, the second collar 18 can be adapted to have a portion of the second collar 18 extend outside of the bulb body 12 when inserted. This portion of the second collar 18 can then be inserted into the tube portion 22, creating a connection between the bulb body 12 and the tube portion 22.

In some implementations, the second collar 18 includes a filter 25 to block particulate matter or fluids from being suctioned into the tube portion 20 upon an application of suction on the adaptor 24 by a human. The filter 25, e.g., a fine mesh of a material, e.g., metal, plastic, or layers of fibrous material, can block particulate matter greater than a particular size. The filter 25 is selected to be operable to substantially block the flow of mucus, and liquid, while enabling for the passing of air from the tip 30 to the adapter 24.

In some implementations, the filter may be located at any position along an airflow path created from just inside the tip of the bulb to an adaptor that is inserted into the human's mouth. For example, in some implementations the filter 25 can be inserted into the lower portion 17 of the bulb body 12. The filter 25 can be of a sufficient radius so as to put pressure on the lower portion 17 of the bulb body 12 when the second collar 18 is inserted. In some implementations, the filter 25 can be inserted into the tube portion 22, and be of a sufficient radius so as to put pressure on the tube portion 22 when the second collar 18 is inserted.

In configurations where the filter 25 is included in the detachable second collar 18, the filter 25 can be removed by a human, e.g., for cleaning or replacement. Other placements may allow for easy removal as required. In some implementations the filter 25 is designed to be cleaned, e.g., by running it under water. In some implementations the filter 25 is a single use only filter, and a human can utilize a new filter 25 upon each application of the aspirator device 10.

In some implementations the second collar 18 includes a one way filter 26 that can substantially inhibit the flow of air being expelled by a human into the aspirator device 10, and allow the flow of air being pushed through the aspirator device into the human, e.g., by atmospheric pressure. The one way filter 26 can be a check valve, e.g., a ball check valve, a diaphragm check valve, a swing check valve, and so on. In this way, a human can apply a suction to a human's, e.g., baby's, nostril without fear of accidentally blowing air into the nostril. Similar to the filter 25, in some implementations, the one way filter 26 can be replaceable by a human.

The tube portion 22 can be substantially 300 mm, 350 mm, or 400 mm long, and created from a deformable material, e.g., the same material as the bulb body 12, plastic, rubber, and can be substantially transparent. In this way the tube portion can be easily checked for cleanliness by a human.

The tube portion 22 receives a connection with the second collar 18, as described above, and also a connection with an adaptor 24 that can be inserted into a human's mouth. In this way the tube portion 22 acts a bridge between the adaptor 24, where the human can create a suction, and the bulb body 12, where particulate matter sucked through the tip 30 can collect.

The adaptor 24, described below in FIG. 5, can include a one way filter 26 in addition to a one way filter 26 included in the second collar 18, or the adaptor 24 can include the sole one way filter 26. Similarly the adaptor can include a filter 25 for blocking the flow of particulate matter, e.g., mucus.

Figure 5:
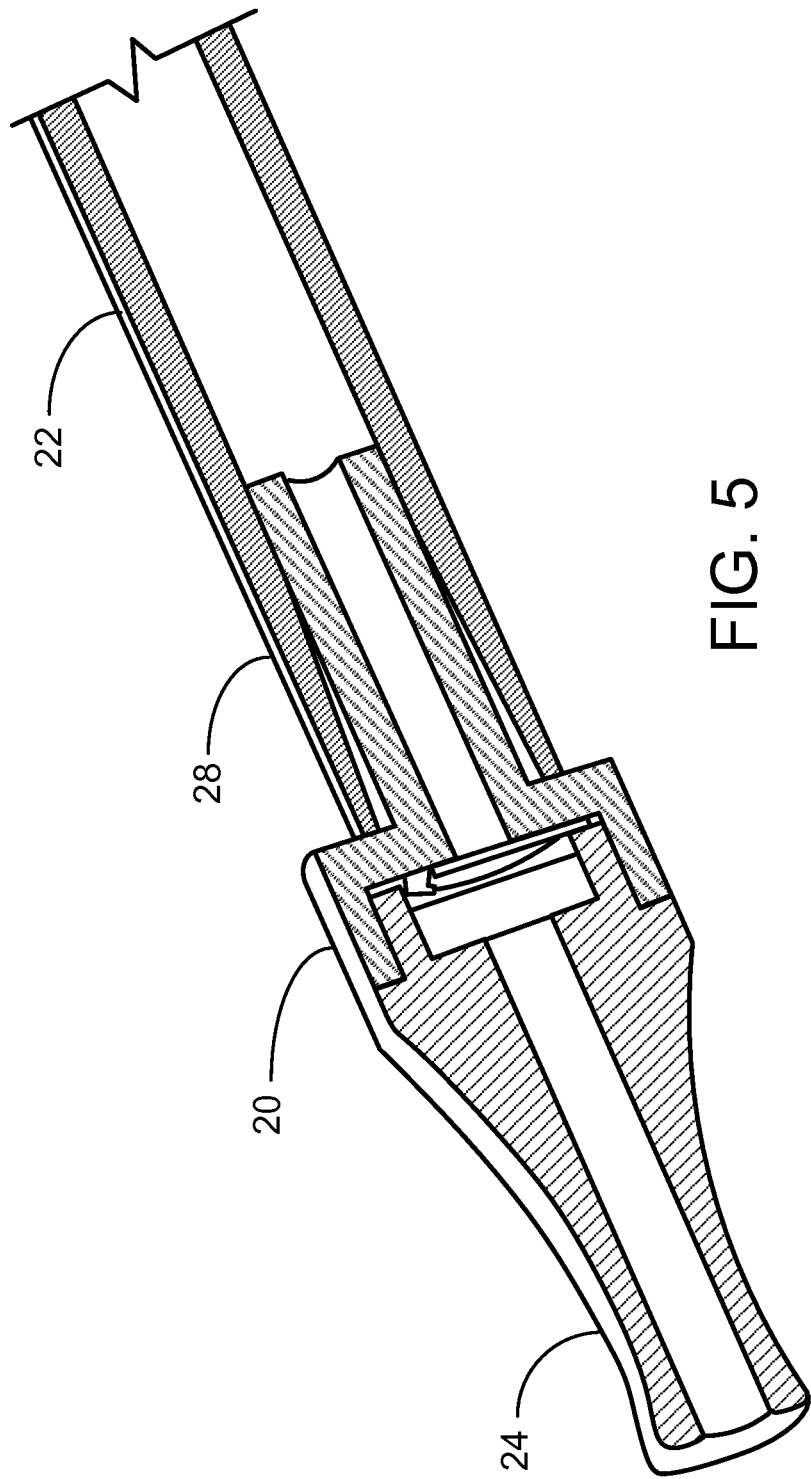
FIG. 5 is a schematic view of an example of the suction adaptor inserted into the tube portion.

FIG. 5 is a schematic view of the adaptor 24 inserted into the tube portion 22. As illustrated, the adaptor 24 includes a one way filter 26, and a sucking tip 27 adapted to a human's mouth. In some implementations the adaptor 24 can include a filter 25 along with, or in addition to, the one way filter 26.

In some implementations, the adaptor 24 can be made from a hard plastic, e.g., poly propylene, and a connector 28 of the adaptor 24 can be inserted into the tube portion 22. The connector 28 can be of a radius greater than a radius of the tube portion 22 to create a pressure between the connector 28 and the tube portion 22 when inserted. Additionally, the length of the connector 28 can be substantially 5 mm, 8 mm, or 10 mm, and can extend that length into the tube portion 22.

The connector 28 of the adaptor 24 can extend from the one way filter 26, e.g., so as to allow for the attachment of the adaptor 24 to the tube portion 22. In some implementations the one way filter 26 can be inserted into the tube portion 22 along with the connector 28, and be of a substantially similar radius as the connector 28. In some implementations the one way filter 26 can be of a greater diameter and include a portion that is adapted for coupling to the tube portion 22.

The sucking tip 27 is configured to allow for the passing of air into a human's mouth, e.g., the adaptor 24 includes a continuous internal hollow portion as illustrated.

In some implementations the sucking tip 27 can be removed from the adaptor 24, so as to replace the one way filter 26, described below in FIG. 6.

Figure 6:
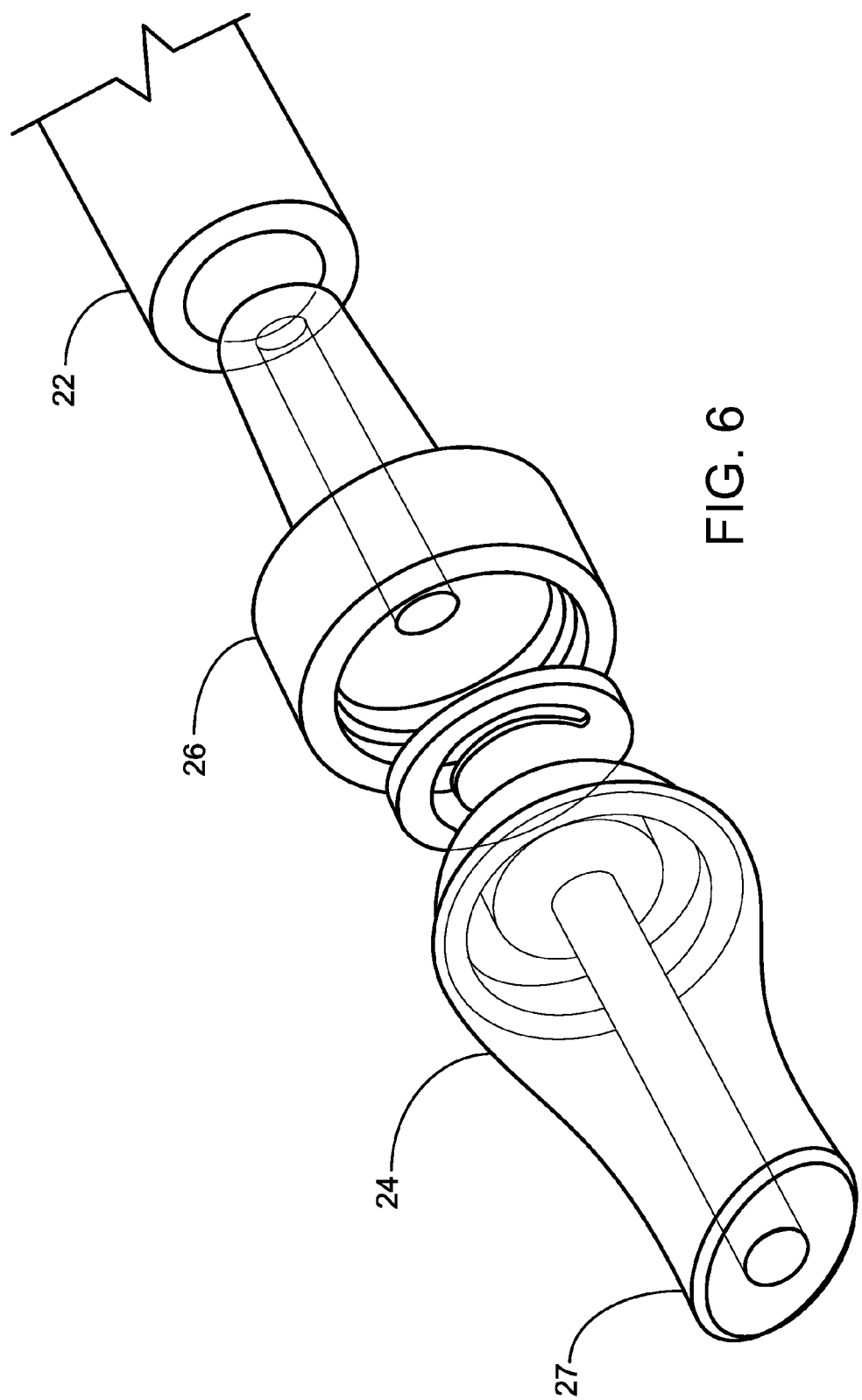
FIG. 6 is a schematic view of an example of the adaptor with the sucking tip taken apart to show the one way valve that prevents a parent from blowing air in to baby's nose Like reference numbers and designations in the various drawings indicate like elements.

FIG. 6 is a schematic view of the adaptor 24 with the sucking tip 27 removed. In some implementations the adaptor 24 can be separated into at least two components, e.g., the sucking tip 27 and one way filter 26.

The sucking tip 27 can connect to the one way filter 27, e.g., by way of internal threads included in the one way filter 27, and external complementary threads included on the sucking tip 27. Twisting the one way filter 27 and sucking tip 27 can result in connection, while an untwist enables separation. In this way the sucking tip 27 can be cleaned or sterilized between uses. In implementations where the adaptor 24 includes a filter 25, separate removal may not be possible, requiring replacement of the adaptor 24 when necessary.

A number of embodiments of the invention have been described. Nevertheless, it will be understood that various modifications may be made without departing from the spirit and scope of the invention. For example, while reference is made to particular connection types, other types of connections are possible (such as other types of sleeves, male/female connections or the like). Similarly, while reference is made to certain types of valves or filters, others are possible (such as slip valves). Further, while reference is made that in certain configurations one or more components of the aspirator allow for separation (such as for cleaning), certain implementations may not include points of separation and instead be formed as unitary structures (such as by molding processes or the like). Accordingly, other embodiments are within the scope of the following claims.

What is claimed is:

1. An aspiration device comprising:
   a bulb aspirator portion including a bulb body having an exterior surface, a first collar, and a tip having an exterior surface, wherein the bulb body includes an upper portion and a lower portion,
   wherein the tip is tapered and angled in shape, has a first end for insertion into a nasal cavity, and a second end configured for detachable connection with a first end of the first collar, and wherein the exterior surface of the bulb body is flush with the exterior surface of the tip;
   a stop configured for detachable connection to the lower portion of the bulb body when in the first configuration; and a suction tube including a second collar, a tube portion and an adaptor, wherein the second collar is disposed at a first end of the suction tube and being adapted to be coupled to the lower portion of the bulb body, wherein the adaptor being coupled to the second end of the suction tube and being configured for insertion into a human mouth to enable suction to be applied at the adaptor so as to enable the application of a suction through the suction tube and into the bulb aspirator when the tube portion is coupled to the bulb aspirator in the second different configuration;

wherein the bulb upper portion is configured for receiving a second end of the first collar, and the bulb lower portion is configured for receiving in a first configuration the stop and in a second different configuration the second collar associated with the suction tube.

2. The aspiration device of claim 1 wherein the second collar includes a first one way filter configured to enable air to flow from the bulb body into the suction tube upon the application of a suction at the adaptor and to substantially inhibit air from being blown from the adaptor into the bulb body.

3. The aspiration device of claim 2 wherein one or both of the second collar or the adaptor includes a second filter for preventing particulate matter from entering a mouth of a user that is applying suction through the adaptor.

4. The aspiration device of claim 3 wherein one or both of the first or second filter are replaceable.

5. The aspiration device of claim 1 wherein the adaptor includes a first one way filter configured to enable air to flow from the bulb body into the suction tube upon the application of a suction at the adaptor and to substantially inhibit air from being blown from the adaptor into the bulb body.

6. The aspiration device of claim 1 wherein the upper portion of the bulb body comprises an internal ridge for detachably locating a portion of the first collar in the bulb body.

7. The aspiration device of claim 6 wherein the first collar includes a first ridge for engaging with the internal ridge of the bulb body so as to enable detachable connection of the first collar to the bulb body.

8. The aspiration device of claim 7 wherein the second end of the tip includes a circumferential recess region for receiving a second ridge of the first collar so as to enable detachable connection of the tip to the first collar.

9. The aspiration device of claim 1 wherein the bulb body is constructed of a deformable material that enables for depressing the bulb body to form a suction at the tip when in the first configuration.

10. The aspiration device of claim 1 wherein the lower portion of the bulb body includes a neck region including a first end in proximity to the suction tube and a second end, wherein the first end of the neck region includes an internal circumferential ridge for maintaining the stop once inserted in the neck when in the first configuration, and a circumferential recess for accepting a ring associated with the stop so as to enable the stop to be maintained with the aspiration device when in the second configuration.

11. The aspiration device of claim 10 wherein the second end of the neck region includes an aperture that is sized less than a diameter of the stop, the aperture being in communication with a one way filter that is disposed in the second collar when deployed in the second configuration.

* * * * *